United States Patent
Ushiro et al.

(10) Patent No.: US 10,912,868 B2
(45) Date of Patent: *Feb. 9, 2021

(54) MEDICAL MATERIAL, MEDICAL SEPARATION MEMBRANE, AND BLOOD PURIFIER

(71) Applicant: Toray Industries, Inc., Tokyo (JP)

(72) Inventors: Suguru Ushiro, Otsu (JP); Akihiro Hayashi, Otsu (JP); Yoshiyuki Ueno, Otsu (JP)

(73) Assignee: Toray Industries, Inc., Tokyo (JP)

( * ) Notice: Subject to any disclaimer, the term of this patent is extended or adjusted under 35 U.S.C. 154(b) by 72 days.

This patent is subject to a terminal disclaimer.

(21) Appl. No.: 16/325,429

(22) PCT Filed: Aug. 22, 2017

(86) PCT No.: PCT/JP2017/029938
§ 371 (c)(1),
(2) Date: Feb. 14, 2019

(87) PCT Pub. No.: WO2018/043209
PCT Pub. Date: Mar. 8, 2018

(65) Prior Publication Data
US 2019/0209744 A1    Jul. 11, 2019

(30) Foreign Application Priority Data
Aug. 31, 2016  (JP) .................. 2016-169559

(51) Int. Cl.
| | | |
|---|---|---|
| *A61L 33/06* | (2006.01) | |
| *A61M 1/34* | (2006.01) | |
| *B01D 71/44* | (2006.01) | |

(52) U.S. Cl.
CPC ............ *A61L 33/06* (2013.01); *A61M 1/34* (2013.01); *A61M 2205/7563* (2013.01); *B01D 71/44* (2013.01)

(58) Field of Classification Search
CPC .................................................. A61L 33/06
See application file for complete search history.

(56) References Cited

U.S. PATENT DOCUMENTS

| | | | | |
|---|---|---|---|---|
| 5,122,582 A | * | 6/1992 | Potthoff-Karl | ......... C08F 6/003 524/808 |
| 10,308,745 B2 | * | 6/2019 | Ushiro | ............... B01D 67/0088 |

(Continued)

FOREIGN PATENT DOCUMENTS

| | | | |
|---|---|---|---|
| EP | 2 724 733 A1 | 4/2014 | |
| GB | 876495 A | * 9/1961 | ................ C08F 8/14 |

(Continued)

OTHER PUBLICATIONS

Young Gyun Kim et al., "Hydrophilic-hydrophobic copolymer nano-sized particle gels: Swelling behavior and dependence on crosslinker chain length", *Fluid Phase Equilibria*, Nov. 10, 2013, vol. 361, No. 10, pp. 200-207.

(Continued)

*Primary Examiner* — Michael F Pepitone
(74) *Attorney, Agent, or Firm* — DLA Piper LLP (US)

(57) ABSTRACT

A medical material is capable of suppressing adhesion of platelets and proteins even when in contact with biological components such as blood for an extended period of time. The medical material is a copolymer including hydrophobic units and hydrophilic units in which the hydrophobic units have a C2-20 terminal alkyl group in a side chain, the static contact angle of water in the copolymer is at least 30° and less than 70°, and the glass transition temperature of the copolymer exists at only one point in the range from 45° C. to less than 90° C.

16 Claims, 3 Drawing Sheets

(56) References Cited

U.S. PATENT DOCUMENTS

| | | | |
|---|---|---|---|
| 2004/0127390 A1 | 7/2004 | Macnab et al. | |
| 2008/0093586 A1 | 4/2008 | Koch et al. | |
| 2011/0017654 A1* | 1/2011 | Ueno | B01D 69/02 210/321.6 |
| 2015/0342860 A1* | 12/2015 | Figura | C11D 1/143 514/772.5 |

FOREIGN PATENT DOCUMENTS

| | | |
|---|---|---|
| GB | 2 043 082 A | 10/1980 |
| JP | 63-053465 A | 3/1988 |
| JP | 5-84290 A | 4/1993 |
| JP | 06-238139 A | 8/1994 |
| JP | 8-254833 A | 10/1996 |
| JP | 2003-320229 A | 11/2003 |
| JP | 2004-059621 A | 2/2004 |
| JP | 4100452 B1 | 6/2008 |
| JP | 4245597 B2 | 3/2009 |
| JP | 2011-072987 A | 4/2011 |
| JP | 5403444 B1 | 1/2014 |
| JP | 5670887 B2 | 2/2015 |
| WO | 2016/158388 A1 | 10/2016 |

OTHER PUBLICATIONS

M. Tijink et al., "Development of novel membranes for blood purification therapies based on copolymers of N-vinylpyrrolidone and n-butylmethacrylate", *Journal of Materials Chemistry B*, Jan. 1, 2013, vol. 1, No. 44 pp. 6066-6077.

Office Action dated Jan. 24, 2020, of counterpart European Application No. 17846214.9.

* cited by examiner

MEDICAL MATERIAL, MEDICAL SEPARATION MEMBRANE, AND BLOOD PURIFIER

TECHNICAL FIELD

This disclosure relates to a medical material, a medical separation membrane and a blood purifier.

BACKGROUND

Conventional medical devices are recognized as contaminants for biological components, and cause adhesion of platelets and proteins, and biological reactions, resulting in serious problems. For example, in conventional blood purifiers such as artificial kidney modules, platelets and proteins adhere to the surfaces of materials in the blood purifier, resulting in deterioration of fractionation performance and water permeability. In addition, stents and artificial blood vessels are required to be semi-permanently continuously used and, therefore, it is important to set specifications to ensure that adhesion of platelets and proteins is suppressed, thus making it possible to withstand use for a long period of time.

Japanese Patent Laid-open Publication No. 2004-59621 discloses a polysulfone-based hydrophilic film in which polyvinylpyrrolidone as a hydrophilic polymer, and the static contact angle of water on a film surface is controlled to 10 degrees or more and 65 degrees or less to suppress contamination.

Japanese Patent Laid-open Publication No. 6-238139 discloses a polysulfone-based polymer separation membrane in which a coating layer insolubilized by radiation crosslinking is formed after the polymer is brought into contact with a hydrophilic polymer solution such as polyvinylpyrrolidone.

Japanese Patent Laid-open Publication No. 2011-72987 discloses a separation membrane containing a water-soluble polymer typified by a copolymer of polyvinylpyrrolidone and polyvinyl acetate, the water-soluble polymer having a glass transition temperature of 90° C. or higher. JP '987 suggests that interaction of a vinyl acetate unit with a hydrophobic base material improves introduction efficiency of the copolymer so that hydrophilization can be efficiently performed.

Japanese Patent No. 4100452 discloses a medical material in which an alkyl (meth)acrylate and a methoxypolyethylene glycol (meth)acrylate copolymer are introduced to a surface thereof, and suggests that the introduction of an alkyl (meth)acrylate and a methoxypolyethylene glycol (meth)acrylate copolymer improves blood compatibility.

However, in JP '621 and JP '139, only hydrophilization of a material surface is performed, and the mobility of a polymer on the material surface is not considered. We prepared the films and separation membranes according to JP '621 and 139, and found that both the films and the separation membranes were poor in suppression of adhesion of platelets and proteins at the time of coming into contact with blood.

In addition, for the separation membrane in JP '987, a vinylpyrrolidone/vinyl acetate copolymer that is a commercially available polymer is used, and a structural design suitable for suppression of adhesion of platelets and proteins is not considered at all. We prepared the separation membrane according to JP '987 and found that proteins adhered to the separation membrane when the separation membrane was in contact with a biological component such as blood for a long period of time.

Further, in the medical material in JP '452, the glass transition temperature of the copolymer is in a range of −100° C. to 20° C. and, therefore, the medical material lacks stability of a polymer form at room temperature, and has a problem in handling property.

Thus, it could be helpful to provide a medical material that is able to suppress adhesion of platelets and proteins even when being into contact with a biological component such as blood.

Proteins contained in a biological component such as blood easily adhere to a hydrophobic surface and, therefore, it is important that the entire contact surface of a medical device has hydrophilicity. This may be because when protein approaches a material surface, the higher order structure of the protein is changed so that the hydrophobic site inside the protein is exposed, and the hydrophobic site hydrophobically interacts with the material surface.

On the other hand, it is known that adhesion of proteins and the like cannot be suppressed when a contact surface of a medical device is coated with a hydrophilic polymer such as polyethylene glycol or polyvinyl alcohol. This may be because when the contact surface of the medical device has excessively high hydrophilicity, the structure of protein is destabilized and, therefore, adhesion of the protein cannot be sufficiently suppressed.

SUMMARY

We found a biological component adhesion-suppressing material that considerably suppresses adhesion of platelets and proteins, and can be used even when in contact with a biological component such as blood for a long period of time, a medical separation membrane using the medical material, and a blood purifier including the medical separation membrane. The medical material, the medical separation membrane and the blood purifier are as follows:

(1) A medical material which is a copolymer comprising a hydrophobic unit and a hydrophilic unit, wherein the hydrophobic unit has a terminal alkyl group having 2 to 20 carbon atoms in a side chain, the static contact angle of water on the copolymer is 30 degrees or more and less than 70 degrees, and the copolymer has only one glass transition temperature in a range of 45° C. or higher and lower than 90° C.

(2) The medical material according to (1), wherein the hydrophobic unit is an alkyl carboxylic acid vinyl ester unit.

(3) The medical material according to (1) or (2), wherein the hydrophilic unit is a vinylpyrrolidone unit.

(4) The medical material according to any one of (1) to (3), wherein the static contact angle of water on the copolymer is 34 degrees or more and less than 50 degrees, and the copolymer has only one glass transition temperature in a range of from 70° C. or higher and lower than 88° C.

(5) A medical separation membrane in which the medical material according to any one of (1) to (4) is bonded or attached to a surface of a membrane including a hydrophobic polymer.

(6) The medical separation membrane according to (5), wherein the static contact angle of water on the hydrophobic polymer is 70 degrees or more and less than 160 degrees, and the glass transition temperature of the hydrophobic polymer is 50° C. or higher and lower than 250° C.

(7) The medical separation membrane according to (5) or (6), wherein the hydrophobic polymer includes a polymer selected from the group consisting of a polysulfone-based polymer, a polymethacrylate-based polymer, a polyacrylate-based polymer, a polyester-based polymer and a polystyrene-based polymer.

(8) A blood purifier including the medical separation membrane according to any one of (5) to (7).

The medical material, the medical separation membrane and the blood purifier is able to suppress adhesion of platelets and proteins even when in contact with a biological component such as blood for a long period of time.

DESCRIPTION OF REFERENCE SIGNS

11: Cover glass
12: Copolymer or hydrophobic polymer
13: Water droplet
14: Interface between copolymer or hydrophobic polymer and water droplet
15: Air
16: Interface between water droplet and air
17: Angle θ
21: DSC curve
22: Extended line of baseline
23: Tangent line of baseline-shifted curve
24: Onset point
41: Tubular case
42: Hollow fiber membrane
43A: Header
43B: Header
44A: Blood-side inlet
44B: Blood-side outlet
45A: Dialysate-side inlet
45B: Dialysate-side outlet
46: Potting agent
47: Hollow fiber membrane module

DETAILED DESCRIPTION

Hereinafter, our materials, membranes and blood purifiers will be described in detail.

Our medical material is a copolymer comprising a hydrophobic unit and a hydrophilic unit. The hydrophobic unit has a terminal alkyl group having 2 to 20 carbon atoms in a side chain. The static contact angle of water on the copolymer is 30 degrees or more and less than 70 degrees. The copolymer has only one glass transition temperature in a range of from 45° C. or higher and lower than 90° C.

The "medical material" means a material used while in contact with a biological component. Examples of the medical material include powder materials, particulate materials, and coating materials bonded or attached to a surface of a medical device, and coating materials are preferable. As a method using such a material as a coating material, mention is made of, for example, a method in which a surface of a separation membrane such as a flat membrane or a hollow fiber membrane is coated with the medical material. Examples of the medical device using the medical material include blood purifiers typified by artificial kidney modules or plasma separators that include the separation membrane, blood circuits, blood storage bags, catheters, stents, contact lenses and biosensors, and blood purifiers are preferable. Examples of the medical device using the medical material further include separation membranes for food and beverage, which are used while in contact with a glycoprotein, and separation membranes to be used for purification of antibody medicaments.

The "biological component" means an organism-derived component substance such as sugar, protein, platelet, or antibody. The biological component is preferably a substance contained in a body fluid such as blood, tear or cerebrospinal fluid and, in particular, a substance contained in blood is preferable as a target.

The "unit" refers to a repeating unit in a homopolymer or copolymer obtained by polymerizing monomers. For example, the carboxylic acid vinyl ester unit refers to a repeating unit in a homopolymer obtained by polymerizing a carboxylic acid vinyl ester monomer, or a repeating unit derived from a carboxylic acid vinyl ester monomer in a copolymer obtained by copolymerizing a carboxylic acid vinyl monomer.

The "hydrophobic unit" is defined as a repeating unit such that a polymer (number average molecular weight: 1,000 or more and 50,000 or less) obtained by polymerizing only the unit is slightly soluble or insoluble in water. The term "slightly soluble or insoluble in water" means that the solubility in 100 g of water at 20° C. is 1 g or less.

The "hydrophilic unit" is defined as a repeating unit such that a polymer (number average molecular weight: 1,000 or more and 50,000 or less) obtained by polymerizing only the unit is easily soluble in water. The term "easily soluble in water" means that the solubility in 100 g of pure water at 20° C. is more than 1 g, preferably 10 g or more.

The "side chain" means a molecular chain branched from the main chain of a unit of a polymer concerned. For example, in a vinyl butyrate unit, the side chain refers to $CH_3CH_2CH_2COO$, and in a methyl methacrylate unit, the side chain refers to $CH_3$ and $CH_3OCO$.

The "terminal alkyl group having 2 to 20 carbon atoms" means a linear, branched or cyclic alkyl group which is present at a terminal of a molecular chain branched from the main chain and which has 2 to 20 carbon atoms. For example, in a vinyl butyrate unit, the terminal alkyl group having 2 to 20 carbon atoms refers to $CH_3CH_2CH_2$, and in the case of a methyl methacrylate unit, the terminal alkyl group having 2 to 20 carbon atoms refers to $CH_3$ and $CH_3$ bonded to (OCO). In addition, the terminal alkyl group having 2 to 20 carbon atoms may be not only a linear alkyl group but also a branched alkyl group or a cyclic alkyl group, but is preferably a linear alkyl group from the viewpoint of availability. The terminal alkyl group is preferably an alkyl group having 2 to 9 carbon atoms because the alkyl group does not have excessively high hydrophobicity, and the terminal alkyl group is more preferably a linear alkyl group having 2 to 9 carbon atoms, still more preferably an alkyl group having 2 to 5 carbon atoms, most preferably a linear alkyl group having 2 to 5 carbon atoms for improving the mobility of the copolymer.

The "number of carbon atoms" refers to the number of carbon atoms that form a functional group concerned, which is a terminal alkyl group in this case. For example, a vinyl acetate ester unit has a terminal alkyl group having 1 carbon atom, a vinyl butyrate ester unit has a terminal alkyl group having 3 carbon atoms, a methyl acrylate unit has a terminal alkyl group having 1 carbon atom, an hexyl acrylate unit has a terminal alkyl group having 6 carbon atoms, and a 1-pentene unit has a terminal alkyl group having 3 carbon atoms.

On the other hand, a 2-hydroxyethyl acrylate unit does not have a terminal alkyl group because an ethylene group is present in the side chain, but is not present at a terminal.

When a plurality of side chain alkyl groups are present in one unit, the "number of carbon atoms" refers to the number of carbon atoms in each alkyl group. In such an example, the unit is considered to have a "terminal alkyl group having 2 to 20 carbon atoms" when at least one of a plurality of side chain alkyl groups has 2 to 20 carbon atoms. For example, an ethyl methacrylate unit has 1 and 2 carbon atoms and, therefore, has a terminal alkyl group having 2 to 20 carbon atoms, but an isopropenyl acetate unit has 1 and 1 carbon atoms and, therefore, does not have a terminal alkyl group having 2 to 20 carbon atoms.

Examples of the hydrophobic unit having a terminal alkyl group having 2 to 20 carbon atoms in the side chain include alkyl carboxylic acid vinyl ester units, acrylic acid alkyl ester units and methacrylic acid alkyl ester units.

The "static contact angle of water" means an angle formed by a polymer-water droplet interface and a water droplet-air interface at the time when a polymer such as a copolymer is deposited in the form of a film, and water droplets are dropped.

A polymer having high hydrophilicity, like polyethylene glycol, polyvinyl alcohol, polyacrylamide or a copolymer composed of such a polymer, has a small water contact angle, which is generally less than 30 degrees. On the other hand, a hydrophobic polymer, like polystyrene, polypropylene or a polymer composed of such a polymer, has a large water contact angle, which is generally 70 degrees or more.

It is important that the above-mentioned copolymer is balanced between hydrophilicity and hydrophobicity. When the hydrophilicity of the polymer is excessively high, the structures of platelets and proteins are destabilized. On the other hand, when the hydrophobicity of the polymer is excessively high, interaction with hydrophobic parts of platelets and proteins occurs, leading to an increase in adhesion. The static contact angle of water on the copolymer is 30 degrees or more and less than 70 degrees, preferably 32 degrees or more and less than 60 degrees, more preferably 34 degrees or more and less than 50 degrees. Any of the preferred lower limits can be combined with any of the preferred upper limits.

The "glass transition temperature" indicates a temperature at which a polymer softens from a glass state to a rubber state, and serves as an index of the mobility of the polymer. A polymer containing a linear alkyl chain, an ethylene glycol chain or a siloxane chain has high mobility and, therefore, sometimes has a glass transition temperature of 30° C. or lower, or 0° C. or lower. On the other hand, a polymer containing a rigid chain such as a naphthyl group or a biphenyl group has low mobility and, therefore, sometimes has a glass transition temperature of 90° C. or higher, or 100° C. or higher.

We believe that when the above-mentioned copolymer has low mobility, platelets and proteins easily adhere to the copolymer because approaching platelets and proteins cannot be repelled. On the other hand, it is not preferable that the copolymer has excessively high mobility, i.e., an excessively low glass transition temperature. When the copolymer has high mobility, not only the structure of protein is destabilized, but also the copolymer itself is deformed or aggregated at room temperature, primary performance of the material cannot be exhibited. The glass transition temperature of the copolymer is 45° C. or higher and lower than 90° C., preferably 50° C. or higher and lower than 89° C., more preferably 70° C. or higher and lower than 88° C. Any of the preferred lower limits can be combined with any of the preferred upper limits. The preferred static contact angle of water and the preferred glass transition temperature can be arbitrarily combined.

The term "having only one glass transition temperature" means that glass transition does not occur at a temperature other than the one glass transition temperature. It is important that the glass transition temperature causes cooperative movement throughout the copolymer. This may be because when there is a distribution in the mobility of the polymer, adhesion of platelets and proteins occurs with a high-mobility site or low-mobility site as an origination point. Therefore, the copolymer is preferably a random copolymer or an alternating copolymer rather than a graft copolymer or a block copolymer.

In addition, for the same reason, it is preferable that there is little deviation in the copolymerization ratio of the copolymer. Specifically, the molar fraction of one type of unit is preferably 5% or more and 95% or less, more preferably 10% or more and 90% or less, still more preferably 20% or more and 80% or less. Any of the preferred lower limits can be combined with any of the preferred upper limits.

The molar fraction of the unit with respect to the entire copolymer can be calculated by nuclear magnetic resonance (NMR) measurement or elemental analysis.

In the medical material, it is more preferable that the static contact angle of water on the copolymer is 34 degrees or more and less than 50 degrees, and the copolymer has only one glass transition temperature of 70° C. or higher and lower than 88° C. When both the static contact angle of water on the copolymer and the glass transition temperature of the copolymer fall within the above-mentioned ranges, respectively, the copolymer is balanced between hydrophilicity and hydrophobicity so that moderate mobility of the copolymer is easily maintained.

When the number average molecular weight of the copolymer is excessively small, it may be impossible to sufficiently exhibit the effect of suppressing adhesion of platelets and proteins and, therefore, the number average molecular weight of the copolymer is preferably 1,000 or more, more preferably 5,000 or more. On the other hand, the upper limit of the number average molecular weight of the copolymer is not particularly limited, but when the number average molecular weight is excessively large, solubility may be reduced and, therefore, the number average molecular weight is preferably 1,000,000 or less, more preferably 500,000 or less, still more preferably 100,000 or less. The number average molecular weight of the copolymer can be measured by gel permeation chromatography (GPC) as described later.

The copolymer may be synthesized by chain polymerization of vinyl monomers or sequential polymerization of difunctional monomers. It is preferable that the copolymer is synthesized by chain polymerization of vinyl monomers because it is easy to adjust the copolymerization ratio of the hydrophobic unit and hydrophilic unit. The vinyl monomer means a monomer having a vinyl group.

The hydrophobic unit is preferably an alkyl carboxylic acid vinyl ester unit. The alkyl carboxylic acid vinyl ester unit refers to a repeating unit in a homopolymer or copolymer obtained by polymerizing a carboxylic acid vinyl ester monomer in which an alkyl group is bonded to a carbon atom of an ester group. In a copolymer containing an alkyl carboxylic acid vinyl ester unit, adhesion of platelets and proteins is suppressed, and biological safety is easily improved.

Examples of the alkyl carboxylic acid vinyl ester unit include propanoic acid vinyl ester units (having 2 carbon atoms in the terminal alkyl group in the side chain), butyric acid vinyl ester units (having 3 carbon atoms in the terminal alkyl group in the side chain), pentanoic acid vinyl ester units (having 4 carbon atoms in the terminal alkyl group in the side chain), pivalic acid vinyl ester units (having 4 carbon atoms in the terminal alkyl group in the side chain), 2-ethylhexanoic acid vinyl ester units (having 7 carbon atoms in the terminal alkyl group in the side chain), and palmitic acid vinyl ester units (having 15 carbon atoms in the terminal alkyl group in the side chain). Among them, propanoic acid vinyl ester units, butyric acid vinyl ester units, pentanoic acid vinyl ester units, pivalic acid vinyl ester units and 2-ethylhexanoic acid vinyl ester units are preferable, propanoic acid vinyl ester units, butyric acid vinyl ester units, pentanoic acid vinyl ester units and pivalic acid vinyl ester units are more preferable, and propanoic acid vinyl ester units and butyric acid vinyl ester units are still more preferable.

The hydrophilic unit is not particularly limited, and examples thereof include methacrylic acid units, acrylic acid units, 2-hydroxyethyl methacrylate units, 2-hydroxyethyl acrylate units, vinylpyrrolidone units, vinyl alcohol units, acrylamide units, alkyl acrylamide units, vinyl amide units and ethylene glycol units. Among them, alkyl acrylamide units, vinyl amide units and vinylpyrrolidone units are preferable because they do not have excessively high hydrophilicity, and easily undergo a polymerization reaction with a carboxylic acid vinyl ester unit, and vinylpyrrolidone units are more preferable because biological safety is more easily improved. The alkyl acrylamide unit refers to a unit in which a hydrogen atom bonded to a nitrogen atom of acrylamide is substituted with an alkyl group. Examples of the alkyl acrylamide unit include N-isopropyl acrylamide units and N,N-dimethyl acrylamide units. On the other hand, examples of the vinyl amide unit include N-vinyl acetamide units and N-methyl-N-vinyl acetamide units.

It is preferable that the hydrophobic unit and the hydrophilic unit do not have an anionic group such as a sulfonic acid group or a cationic group such as an amino group. This is because anionic groups and cationic groups may activate and degenerate biological components through complement activation. On the other hand, nonionic groups such as amide groups, ester groups and ether groups are capable of further reducing influences on the living body and, therefore, it is preferable that the hydrophobic unit and the hydrophilic unit preferably have such nonionic groups. In the above-mentioned copolymer, the preferred hydrophobic unit and the preferred hydrophilic unit described above can be arbitrarily combined. For example, it is preferable that the hydrophobic unit is an alkyl carboxylic acid vinyl ester unit, and the hydrophilic unit is a vinylpyrrolidone unit. In addition, the hydrophobic unit and the hydrophilic unit may be an acrylic acid alkyl ester unit and an acrylamide unit or an alkyl acrylamide unit, respectively.

It is preferable that the copolymer is dissolved in any of water, ethanol and isopropanol in an amount of 10% by weight or more. This means that the copolymer does not have excessively high hydrophobicity, adhesion of platelets and proteins is small, and at the time when a copolymer is dissolved in a solution, and molded, it is possible to prepare a solution having a reduced impact on biological components.

The copolymer may be amorphous or crystalline, but when the copolymer is crystalline, the adhesion suppressing effect of platelets and proteins varies depending on the higher order structure of the copolymer so that it may be necessary to control the structure. Therefore, the copolymer is preferably amorphous. The "crystallinity" means that crystals are formed at a temperature equal to or lower than the melting point at the time when the copolymer in a molten state is cooled. Examples of the crystalline polymer include polyethylene and polyethylene terephthalate. The term "amorphous" means that crystals are not formed. Examples of the amorphous polymer include polyvinyl acetate, polyvinyl butyrate and polyvinylpyrrolidone.

The copolymer may be nonbiodegradable or biodegradable, but the copolymer may have poor long-term storage stability when the copolymer is biodegradable and, therefore, the copolymer is preferably nonbiodegradable. The term "biodegradable" means that the copolymer is decomposed by microorganisms. Examples of biodegradable polymer include polylactic acid. The term "nonbiodegradable" means that the copolymer is not decomposed by microorganisms. Examples of the nonbiodegradable polymer include polyvinyl hexanoate, polyvinyl butyrate and polyvinylpyrrolidone.

Other monomers, e.g., monomers containing a reactive group such as a hydroxy group, a carboxy group or glycidyl group may be copolymerized within the bounds of not hindering the action/function of the copolymer.

The copolymer can be synthesized by a chain polymerization method typified by, for example, a radical polymerization method using an azo-based initiator, but the synthesis method is not limited thereto.

The copolymer is produced by, for example, the following production method, but the production method is not limited thereto.

A monomer is mixed with a polymerization solvent and a polymerization initiator, and the mixture is mixed with stirring in a nitrogen atmosphere at a predetermined temperature for a predetermined period of time to carry out polymerization reaction. The reaction liquid is cooled to room temperature to stop the polymerization reaction, and put in a solvent such as hexane. A copolymer can be obtained by recovering a precipitated precipitate, and drying the recovered precipitate under reduced pressure.

The reaction temperature of the polymerization reaction is preferably 30 to 150° C., more preferably 50 to 100° C., still more preferably 70 to 80° C.

The pressure of the polymerization reaction is preferably atmospheric pressure.

The reaction time of the polymerization reaction is appropriately selected according to conditions such as a reaction temperature, but is preferably 1 hour or more, more preferably 3 hours or more, still more preferably 5 hours or more. When the reaction time is short, a large amount of an unreacted monomer may remain in the polymer. On the other hand, the reaction time is preferably 24 hours or less, more preferably 12 hours or less. When the reaction time is long, side reactions such as production of a dimer formation may easily occur, thus making it difficult to control the molecular weight.

The polymerization solvent to be used in the polymerization reaction is not particularly limited as long as it is a solvent compatible with a monomer and, for example, an ether-based solvent such as dioxane or tetrahydrofuran, an amide-based solvent such as N,N-dimethylformamide, a sulfoxide-based solvent such as dimethylsulfoxide, an aromatic hydrocarbon-based solvent such as benzene or toluene, an alcohol-based solvent such as methanol, ethanol, isopropyl alcohol, amyl alcohol or hexanol, water or the like is used, but from the viewpoint of toxicity, it is preferable to use an alcohol-based solvent or water.

As the polymerization initiator for the polymerization reaction, for example, a photopolymerization initiator or a thermal polymerization initiator is used. A polymerization initiator that generates any of a radical, a cation and an anion may be used, but a radical polymerization initiator is preferably used because it hardly causes decomposition of a monomer. As the radical polymerization initiator, for example, an azo initiator such as azobisisobutyronitrile, azobisdimethylvaleronitrile or dimethyl azobis(isobutyrate), or a peroxide initiator such as hydrogen peroxide, benzoyl peroxide, di-tert-butyl peroxide or dicumyl peroxide is used.

The solvent in which a polymerization reaction is put after polymerization reaction is stopped is not particularly limited as long as it is a solvent in which the copolymer is precipitated and, for example, a hydrocarbon-based solvent such as pentane, hexane, heptane, octane, nonane or decane, or an ether-based solvent such as dimethyl ether, ethyl methyl ether, diethyl ether or diphenyl ether is used.

The static contact angle of water on the copolymer is measured by a droplet method as described later. For example, when the static contact angle of water on the copolymer is measured by the droplet method, the following procedure is carried out. The copolymer is dissolved in chloroform, and a 1 wt % solution is prepared. A cover glass having a size of 2 cm×2 cm (symbol 11 in FIG. 1) is spin-coated at 1000 rpm for 30 seconds to apply a copolymer as shown by symbol 12 in FIG. 1. Using an automatic contact angle meter, the contact angle with pure water 2 seconds after water deposition is analyzed with an image by a curve fitting method to determine an angle θ (17) formed by an interface (14) between a copolymer (12) and a water droplet (13) at the water droplet end portion and an interface (16) between the water droplet (13) and air (15). Care is needed because the copolymer may be dissolved in pure water when the time after water deposition increases. One sample is measured at three points in air at 25° C., and the average of the angle θ is calculated as a static contact angle of water on the copolymer.

Figure 2:
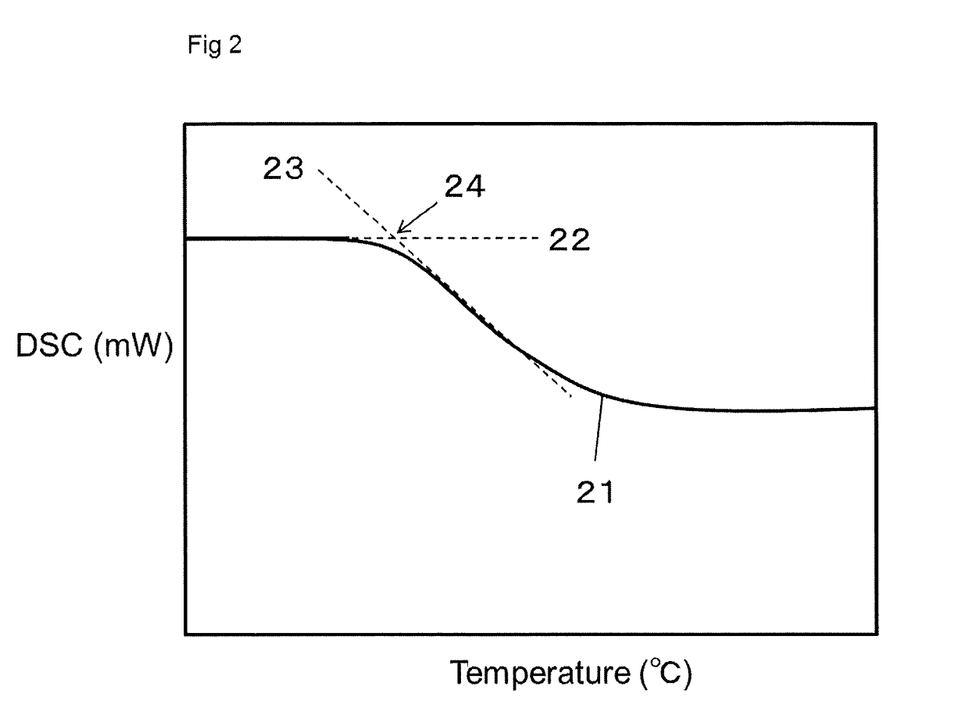
FIG. 2 is a schematic diagram showing a DSC curve and a glass transition temperature.

The glass transition temperature is measured by differential scanning calorimetry (DSC) as described later. For example, when the glass transition temperature of the copolymer is measured by DSC, the following procedure is carried out. Approximately 10 mg of the copolymer is placed in an aluminum sample container, and the container is hermetically sealed to obtain a measurement sample. As a reference, an empty aluminum container is prepared. A heating process and a cooling process are each carried out 2 cycles. Symbol 21 in FIG. 2 denotes a DSC curve and, in FIG. 2, the abscissa represents a temperature of the sample container, and the ordinate represents a difference DSC (mW) between the amount of heat applied to the measurement sample and the amount of heat applied to the reference per unit time. An onset point (24), which is an intersection of an extended line (22) of the baseline of the DSC curve and a tangent line (23) of a baseline-shifted curve, in the heating process in the second cycle is defined as a glass transition temperature of the polymer.

In addition, in the medical separation membrane, the medical material is bonded or attached to a surface of a membrane including a hydrophobic polymer.

The "separation membrane" means a membrane that selectively removes a specific substance contained in a liquid to be treated such as blood or an aqueous solution, by adsorption or on the basis of the size of a substance. As a form of the separation membrane, mention is made of a flat membrane, a hollow fiber membrane and the like, but the medical separation membrane is preferably a hollow fiber membrane from the viewpoint of blood purification efficiency.

There are various methods of using the medical material, but it is preferable that the medical material is bonded or attached to a surface of a membrane including a hydrophobic polymer. That is, when the medical material is bonded or attached to a surface in contact with a biological component such as blood, an effect of suppressing adhesion of platelets and proteins is exhibited. The surface in contact with a biological component refers to an outermost surface which is in contact with a biological component such as blood, and extends to a depth of 10 nm.

The medical material may be used alone as a medical separation membrane, but when the medical material has high hydrophilicity, the medical material may be eluted in blood or the like and, therefore, it is preferable that the medical material is made compatible with or bonded or attached to a surface of a hydrophobic polymer, a metal or the like when used. In particular, a hydrophobic polymer is easily molded, and easily bonded or attached to the medical material, and has little risk of being eluted and, therefore, it is preferable that the medical material is, for example, bonded or attached to a surface of a membrane including a hydrophobic polymer.

Whether the medical material is bonded or attached to a surface of a membrane including a hydrophobic polymer can be determined by surface analysis such as XPS measurement or TOF-SIMS measurement.

The "hydrophobic polymer" refers to a polymer having a solubility of 1 g or less in 100 g of pure water at 20° C.

The term "bonded or attached to" means that a signal derived from a copolymer in a medical material concerned is detected in compositional analysis and the like. For example, when a carbon peak derived from an ester group is detected in analysis of a surface, at which an ester group-containing copolymer is present, by X-ray photoelectron spectroscopy (XPS), the copolymer is present. Since the copolymer is present at a surface in contact with a biological component, it is preferable to detect the copolymer by performing analysis by XPS or time-of-flight secondary ion mass spectrometry (TOF-SIMS). When analysis is performed by a plurality of methods, it is determined that the medical material is "bonded or attached to" the membrane when a signal derived from the copolymer in the medical material concerned is detected by at least one of the above-mentioned methods.

To reduce elution of the hydrophobic polymer in blood or the like, the static contact angle of water on the hydrophobic polymer is preferably 70 degrees or more and less than 160 degrees, more preferably 80 degrees or more and less than 140 degrees, still more preferably 90 degrees or more and less than 120 degrees. Any of the preferred lower limits can be combined with any of the preferred upper limits. In addition, to ensure that the copolymer is easily made compatible with, or bonded or attached to the membrane, a difference between the static contact angle of water on the copolymer and the static contact angle of water on the hydrophobic polymer is preferably less than 100 degrees, more preferably less than 90 degrees, still more preferably less than 80 degrees.

When the hydrophobic polymer has a low glass transition temperature, it may be impossible to maintain sufficient strength. On the other hand, when the hydrophobic polymer has an excessively high glass transition temperature, the solubility and moldability of the polymer are deteriorated.

The glass transition temperature of the hydrophobic polymer is preferably 50° C. or higher and lower than 250° C., more preferably 70° C. or higher and lower than 200° C., still more preferably 90° C. or higher and lower than 150° C. Any of the preferred lower limits can be combined with any of the preferred upper limits.

In the medical separation membrane, it is preferable that the static contact angle of water on the hydrophobic polymer is 70 degrees or more and less than 160 degrees, and the glass transition temperature of the hydrophobic polymer is 50° C. or higher and lower than 250° C. This is because when both the static contact angle of water on the hydrophobic polymer and the glass transition temperature of the hydrophobic polymer fall within the above-mentioned ranges, respectively, it is possible to prevent elution in blood or the like and secure sufficient mechanical strength.

Preferably, the hydrophobic polymer includes a polymer selected from the group consisting of a polysulfone-based polymer, a polymethacrylate-based polymer, a polyacrylate-based polymer, a polyester-based polymer and a polystyrene-based polymer. The polysulfone-based polymer is a polymer having an aromatic ring, a sulfonyl group and an ether group in the main chain, and examples thereof include polysulfone, polyether sulfone and polyaryl ether sulfone. Examples of the polymethacrylate-based polymer include polymethyl methacrylate and polyhexyl methacrylate. Examples of the polyacrylate-based polymer include polyethyl acrylate and polyoctyl acrylate. Examples of the polyester-based polymer include polyethylene terephthalate and polybutylene terephthalate. Examples of the polystyrene-based polymer include polystyrene, poly(p-methylstyrene) and poly-α-methylstyrene.

In particular, the polysulfone-based polymer is preferably used because it has favorable moldability, and is easily bonded or attached to the medical material.

As the main raw material of the membrane including the hydrophobic polymer, for example, a polysulfone-based polymer represented by the chemical formula of formula (1) and/or (2) is preferably used, but the main raw material of the membrane is not limited thereto. In the formulae, n is an integer of 1 or more, preferably 30 to 100, more preferably 50 to 80. When n has a distribution, the average of the distribution is defined as n. The "main raw material" means a raw material contained in an amount of 90% by weight or more based on the total of the medical separation membrane.

In the formulae, n represents an integer of 1 or more.

The polysulfone-based polymer that can be used for the medical separation membrane is preferably a polymer composed only of a repeating unit represented by formula (1) and/or (2), but may be a copolymer obtained by copolymerization with a monomer other than the monomer derived from the repeating unit represented by formula (1) and/or (2), or a modified product thereof. The copolymerization ratio of the above-mentioned other monomer in the copolymer obtained by copolymerization with the above-mentioned other monomer is preferably 10% by weight or less based on the total of the polysulfone-based polymer.

Examples of the polysulfone-based polymer that can be used for the medical separation membrane include polysulfone-based polymers such as Udel Polysulfone P-1700 and P-3500 (manufactured by Solvay), Ultrason (registered trademark) S3010 and S6010 (manufactured by BASF SE), VICTREX (manufactured by Sumitomo Chemical Co., Ltd.), Radel (registered trademark) A (manufactured by Solvay) and Ultrason (registered trademark) E (manufactured by BASF SE).

Since the hydrophobic polymer has high hydrophobicity, a hydrophilic polymer may be further included in the separation membrane in addition to the copolymer to obtain a medical separation membrane. The hydrophilic polymer may be included during molding of the medical separation membrane or after molding of the medical separation membrane.

Preferably, the hydrophilic polymer contains an amide bond in the structure of the repeating unit of the hydrophilic polymer.

Examples of the hydrophilic polymer containing an amide bond include polyvinyl caprolactam, polyvinylpyrrolidone, polyvinyl acetamide, polyacrylamide and derivatives thereof. Among them, polyvinylpyrrolidone is preferably used because it has favorable moldability and spinnability with a polysulfone-based polymer, and also serves as a pore forming agent in formation of a hollow fiber membrane.

The "hydrophilic polymer" is a polymer having a solubility of more than 1 g, preferably 10 g or more, in 100 g of pure water at 20° C.

Presence of a hydrophilic polymer containing an amide bond can be confirmed by, for example, observing a peak in a range of 1617 to 1710 $cm^{-1}$ in ATR-IR measurement.

The medical material may be used as a powder material or a fine particle material, or used as a coating material to be bonded or attached to a surface of a medical device such as a separation membrane such as a flat membrane or a hollow fiber membrane. For example, a flat membrane of polyethylene terephthalate to be used for an artificial blood vessel or the like is immersed in an aqueous solution of a copolymer as a medical material, radiation exposure is performed to crosslink and immobilize the medical material, and the thud-obtained product is used as a medical separation membrane. From the viewpoint of suppressing adhesion of platelets, the concentration of the aqueous solution of the copolymer is preferably 0.01 ppm or more, more preferably 0.1 ppm or more. The number of adhering platelets is preferably 20 or less, more preferably 10 or less per area of $4.3 \times 10^3$ $\mu m^2$. The number of adhering platelets can be measured by a method as described later. In addition, in a blood circuit, it is preferable to use the blood circuit with a medical material bonded or attached to an inner surface of a tube or the like that forms the circuit, the inner surface being mainly in contact with blood or the like. In a catheter, stent or the like, a medical material may be bonded or attached to a surface of a (metal) material, which is mainly in contact with blood or the like.

In addition, it is preferable that as one component that forms a medical separation membrane, the medical material is bonded or attached to a surface of the membrane (particularly, an inner surface which is frequently brought into blood) to suppress adhesion of blood components.

In addition, we provide a medical device, particularly a blood purifier that includes the medical separation membrane. That is, the blood purifier includes the medical separation membrane.

The "blood purifier" refers to a product having a medical separation membrane aimed at removing wastes and harmful substances in blood by circulating blood outside the body. Examples of blood purifiers include artificial kidney modules to be used for treatment of chronic renal failure, continuous blood flow blood purifiers to be used for treatment of acute renal failure, and exotoxin adsorption columns.

The "module" means a device included in a casing. For example, the medical separation membrane module is a device in which a medical separation membrane is included in a casing.

The blood purifier is used while in contact with blood for a long period of time, e.g., about 4 hours in an artificial kidney module used for treatment of chronic renal failure and 1 day to several days for a continuous blood purifier used for treatment of acute renal failure. Thus, adhesion of platelets and proteins occurs, resulting in deterioration of fractionation performance and water permeability. Further, since the artificial kidney module and the continuous blood purifier are subjected to filtration from the inside to the outside of the hollow fiber membrane for removing wastes and harmful substances in blood, adhesion of platelets and proteins particularly easily occurs.

As a method of binding or attaching the copolymer to the medical separation membrane, for example, a method in which a copolymer is bonded or attached after formation of a membrane is preferable, and a method in which a copolymer in the form of a solution (aqueous solution) is brought into contact with a surface of a membrane is used. More specific examples include a method in which a copolymer solution is caused to flow at a predetermined flow rate, and a method in which a membrane is immersed in the solution. In addition, mention is also made of a method in which conditions are set so that a copolymer is intentionally put together on a membrane surface in a method in which a copolymer is added to a dope solution to form a membrane, and the mixture is spun.

There are various methods of producing the medical separation membrane module, depending on the use of the separation membrane module. As one aspect thereof, the method can be divided into a step of producing a medical separation membrane and a step of incorporating the medical separation membrane into a module. In production of the medical separation membrane module, treatment by radiation exposure may be performed before the step of incorporating the medical separation membrane into a module, or may be performed after the step of incorporating the medical separation membrane into a module. Since the medical separation membrane module is for medical use, it is preferable to perform treatment by γ ray irradiation as treatment by radiation exposure after the step of incorporating the separation membrane into a module because sterilization can be performed at the same time.

Figure 3:
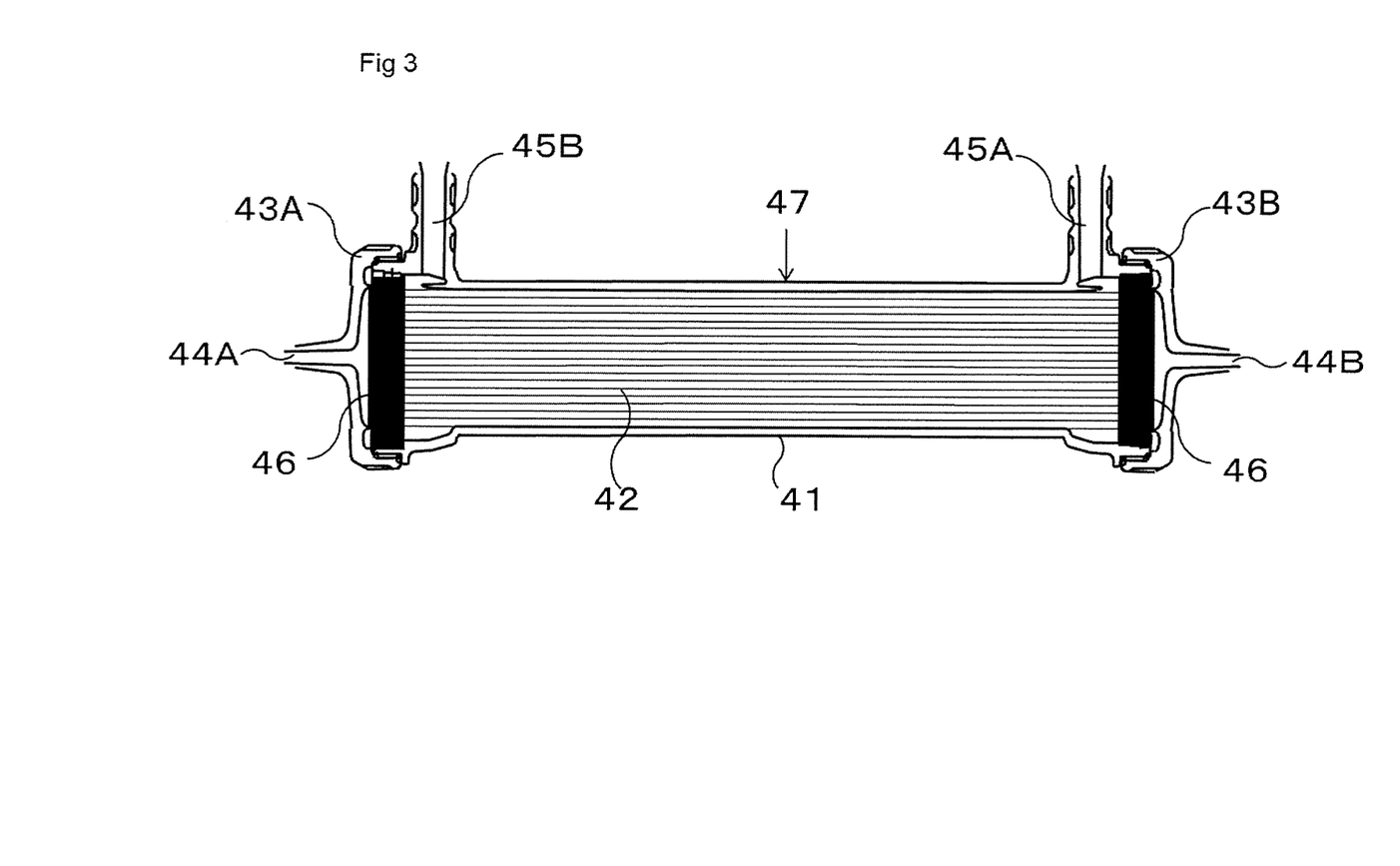
FIG. 3 is a schematic view of a hollow fiber membrane module.

FIG. 3 is a schematic view showing a cross-section of a hollow fiber membrane module (47) as one form of the medical separation membrane module, the cross-section being horizontal to a longitudinal direction. The hollow fiber membrane module has a structure in which a plurality of hollow fiber membranes (42) cut to a predetermined length are present in a tubular case (41) while being bundled, and both ends of the hollow fiber membranes are put together with a potting agent (46), respectively. Both end portions of the hollow fiber membrane (42) are open. Headers (43A and 43B) are placed at both ends of the hollow fiber membrane module, respectively, and the header has a hollow fiber membrane blood-side inlet (44A) and a hollow fiber membrane blood-side outlet (44B). In addition, the tubular case (41) has a hollow fiber membrane dialysate-side inlet (45A) and a hollow fiber membrane dialysate-side outlet (45B).

As a specific example of a method of producing a medical separation membrane module, one example of a method of producing a hollow fiber membrane module to be used in a blood purifier will be described.

Examples of the method of producing a hollow fiber membrane to be incorporated into a blood purifier include the following method. That is, polysulfone and polyvinylpyrrolidone (weight ratio of preferably 20:1 to 1:5, more preferably 5:1 to 1:1) is dissolved in a mixed solvent of a good solvent (preferably N,N-dimethylacetamide, dimethylsulfoxide, N,N-dimethylformamide, N-methylpyrrolidone, dioxane or the like) and a poor solvent (preferably water, ethanol, methanol, glycerin or the like) for polysulfone to obtain a dope solution (concentration of preferably 10 to 30% by weight, more preferably 15 to 25% by weight), and at the time of discharging the dope solution from a double ring-shaped die, a bore fluid is fed to the inside, and the dope solution is run through a dry section, and then guided to a coagulation bath. Since the humidity of the dry section affects the dope solution, the phase separation behavior in the vicinity of the outer surface is accelerated by supplying moisture from the outer surface of the membrane during running of the dry section so that the pore diameter can be increased, resulting in reduction of permeation/diffusion resistance in dialysis. However, when the relative humidity is excessively high, coagulation of the dope solution on the outer surface is dominant so that the pore diameter tends to rather decrease, resulting in increase of permeation/diffusion resistance in dialysis. Therefore, the relative humidity is preferably 60 to 90%. In addition, it is preferable to use a bore fluid having a composition based on the solvent used for the dope solution from the viewpoint of process suitability. For example, when N,N-dimethylacetamide is used, an aqueous solution with a bore fluid concentration of preferably 45 to 80% by weight, more preferably 60 to 75% by weight is used.

The good solvent means a solvent in which a target polymer is soluble in an amount of 10% by weight or more at 20° C. The poor solvent means a solvent in which a target polymer is soluble in an amount of less than 10% by weight at 20° C.

The method of incorporating the hollow fiber membrane into the module is not particularly limited, but, for example, there are the following methods. First, the hollow fiber membrane is cut to a required length and a required number of pieces are bundled and placed in a cylindrical case. Both ends of the case are then temporarily capped, and a potting agent is placed at both ends of the hollow fiber membrane. A method in which the potting agent is placed while the module is rotated with a centrifuge is a preferred method because the potting agent is uniformly packed. After the potting agent is solidified, the hollow fiber membrane is cut at both end portions to be opened at both ends so that a hollow fiber membrane module is obtained.

The polysulfone-based polymer used as a main raw material of the hollow fiber membrane generally has high hydrophobicity and, therefore, when the polysulfone-based polymer is used as a hollow fiber membrane as it is, adhesion of organic substances such as proteins easily occurs. Thus, a hollow fiber membrane obtained by introducing the copolymer into the inner surface is preferably used. In particular, from the viewpoint of improving the hydrophilicity of the inner surface, a copolymer containing a carboxylic acid vinyl ester unit is preferably used. Examples of the method of bonding or attaching the copolymer to the inner surface include a method in which a solution of the copolymer is brought into contact with a hollow fiber membrane in the module, and a method in which at the time of spinning the hollow fiber membrane, a bore fluid containing the copolymer is brought into contact with the inside of the hollow fiber membrane.

When an aqueous solution of the copolymer is fed through the hollow fiber membrane in the module, and bonded or attached to the surface, a sufficient amount of the copolymer is not bonded or attached to the surface when the concentration of the copolymer in the aqueous solution is excessively low. Therefore, the copolymer concentration in the aqueous solution is preferably 10 ppm or more, more preferably 100 ppm or more, still more preferably 300 ppm or more. When the concentration of the copolymer in the aqueous solution is excessively large, the amount of an eluate from the module may increase and, therefore, the copolymer concentration in the aqueous solution is preferably 100,000 ppm or less, more preferably 10,000 ppm or less.

When the copolymer is not dissolved in water at a predetermined concentration, the copolymer may be dissolved in a mixed solvent of water and an organic solvent in which the hollow fiber membrane is insoluble, or an organic solvent compatible with water and in which the hollow fiber membrane is insoluble. Examples of the organic solvent that can be used for the organic solvent or the mixed solvent include, but are not limited to, alcohol-based solvents such as methanol, ethanol and propanol.

In addition, when the ratio of the organic solvent in the mixed solvent increases, the hollow fiber membrane may be swollen, leading to reduction of strength. Therefore, the weight fraction of the organic solvent in the mixed solvent is preferably 60% or less, more preferably 10% or less, still more preferably 1% or less.

Further, from the viewpoint of improving the hydrophilicity of the hollow fiber membrane as a whole, it is preferable that a polysulfone-based polymer and a hydrophilic polymer are mixed, and the mixture is spun.

To prevent elution of the bonded or attached copolymer at the time of use, it is preferable that the copolymer is insolubilized by radiation exposure or heat treatment after being bonded or attached to the surface.

For the radiation exposure, an α-ray, a β-ray, a γ-ray, an X-ray, an ultraviolet ray, an electron beam or the like can be used. Blood purifiers such as artificial kidneys are obliged to be sterilized prior to shipping, and in recent years, a radiation sterilization method using a γ ray or an electron beam has been heavily used from the viewpoint of the low residual toxicity and convenience. Therefore, it is preferable that a radiation sterilization method is used while an aqueous solution in which the copolymer is dissolved is in contact with the hollow fiber membrane in the medical separation membrane module because insolubilization of the copolymer can be achieved in parallel to sterilization.

When the medical device is sterilized and reformed at the same time, the irradiation dose of a radiation is preferably 15 kGy or more, more preferably 25 kGy or more. This is because an irradiation dose of 15 kGy or more is effective for sterilizing a blood purification module or the like with a γ-ray. In addition, the irradiation dose is preferably 100 kGy or less. This is because when the irradiation dose is more than 100 kGy, the copolymer may easily undergo three-dimensional crosslinking, decomposition or the like, leading to deterioration of blood compatibility.

An antioxidant may be used to suppress crosslinking reaction in radiation exposure. The antioxidant means a substance having a property of easily giving electrons to other molecules, and examples thereof include, but are not limited to, water-soluble vitamins such as vitamin C, polyphenols, and alcohol-based solvents such as methanol, ethanol and propanol. These antioxidants may be used singly, or in combination of two or more thereof. When an antioxidant is used for the medical separation membrane module, it is necessary to take safety into consideration, and therefore an antioxidant having low toxicity such as ethanol or propanol is preferably used.

In a blood purifier such as an artificial kidney module, not only fractionation performance and permeability may be deteriorated due to adhesion of platelets and proteins, but also it may be impossible to continue extracorporeal circulation because blood cannot flow into the hollow fiber membrane due to blood coagulation. For adhesion of platelets and proteins to the inside of the hollow fiber membrane, the performance of the hollow fiber membrane can be evaluated by measuring the relative adhesion amount of total proteins to the inner surface of the hollow fiber membrane after circulation of blood.

Deterioration of the performance of the blood purifier is related particularly to adhesion of proteins, and the smaller the relative adhesion amount of total proteins, the less the performance deterioration.

The relative adhesion amount of total proteins can be measured by a method as described later. To prevent blood-dependent variations in the adhesion amount of total proteins, measurement of the hollow fiber membrane in Artificial Kidney Toraylight (registered trademark) CX manufactured by Toray Industries, Inc. is performed in parallel as a control, and the adhesion ratio (%) relative to the control is calculated.

Adhesion of platelets and proteins to a medical device to be used for a long period of time occurs markedly within 60 minutes after the medical device comes into contact with blood and, therefore, the performance of the medical device can be evaluated by measuring the relative adhesion amount of total proteins after circulation of blood for 60 minutes. From the viewpoint of suppressing performance deterioration, the relative adhesion amount of total proteins to the medical device is preferably 40% or less, more preferably 30% or less, still more preferably 20% or less.

EXAMPLES

Our materials, membranes and blood purifiers will be illustrated below with reference to Examples, but it should be understood that this disclosure is not construed as being limited thereto.

Evaluation Method (1) Number Average Molecular Weight

A 0.1 N $LiNO_3$ solution of water/methanol=50/50 (volume ratio) was prepared, and used as a GPC development solution. 2 mg of the polymer was dissolved in 2 ml of this solution. 100 μL of the polymer solution was injected into a GPC connected to a column ($GMPW_{XL}$ manufactured by TOSOH CORPORATION, inner diameter: 7.8 mm×30 cm, particle size: 13 μm). The device configuration of GPC is as follows:

Pump: LC-20AD
Autosampler: SIL-20AHT
Column oven: CTO-20A.

The flow rate was 0.5 mL/min, and the measurement time was 30 minutes. Detection was performed using a differential refractive index detector RID-10A (manufactured by Shimadzu Corporation), and the number average molecular weight was calculated from a peak derived from the polymer, which appeared around an elution time of 15 minutes. The number average molecular weight was calculated while being rounded off from the tenth decimal place. A polyethylene oxide standard sample (0.1 kD to 1258 kD) manufactured by Agilent Company was used for preparation of a calibration curve.

(2) Molar Fraction of Hydrophilic Unit 2 mg of the copolymer was dissolved in 2 ml of chloroform-D (99.7%) (Wako Pure Chemical Industries, Ltd., 0.05V/V %, with TMS), and the solution was added in a NMR sample tube, and subjected to NMR measurement (Superconducting FTNMR EX-270: manufactured by JEOL Ltd.). The temperature was room temperature, and the cumulative number was 32. From the result of this measurement, the value of $A_{PVP}/(A_{PVP}+A_{VC})\times100$ was calculated as a molar fraction of the hydrophilic unit where the area of a region surrounded a base line and a peak observed in a range of 2.7 to 4.3 ppm and derived from a proton (3H) bonded to a carbon atom adjacent to a nitrogen atom in vinylpyrrolidone is $3A_{PVP}$, and the area of a region surrounded by a base line and a peak observed in a range of 4.3 to 5.2 ppm and derived from a proton (1H) bonded to carbon at the α-position in vinyl carboxylate is $A_{VC}$. This method is an example of calculating the molar fraction in a copolymer of vinylpyrrolidone and a carboxylic acid vinyl ester, and in a copolymer including a combination of other monomers, an appropriate proton-derived peak is selected, and the molar fraction is determined. The molar fraction was calculated while being rounded off from the ones place.

(3) Static Contact Angle of Water

Copolymer or hydrophobic polymer (hereinafter, collectively referred to as a polymer) was dissolved in chloroform (manufactured by Wako Pure Chemical Industries, Ltd.) to prepare a 1 wt % solution. A cover glass having a size of 2 cm×2 cm (symbol 11 in FIG. 1) was spin-coated at 1000 rpm for 30 seconds to apply a polymer as shown by symbol 12 in FIG. 1.

Figure 1:
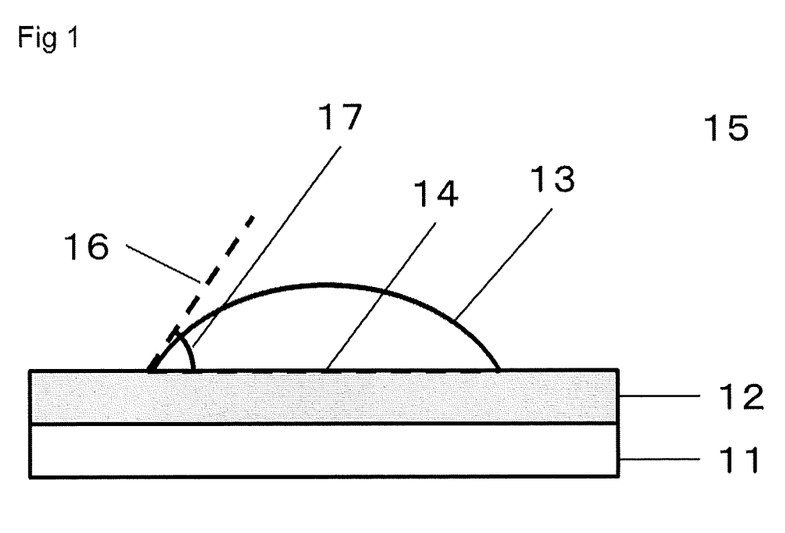
FIG. 1 is a schematic diagram showing measurement of a static contact angle of water.

Using an automatic contact angle meter Drop Master DM 500 (manufactured by Kyowa Interface Science Co., LTD.), the contact angle with pure water 2 seconds after water deposition was analyzed with an image by a curve fitting method to determine an angle θ (17) formed by an interface (14) between a polymer (12) and a water droplet (13) at the water droplet end portion and an interface (16) between the water droplet (13) and air (15). Care is needed because the polymer may be dissolved in pure water when the time after water deposition increases. One sample was measured at three points in air at 25° C., and the average of the angle θ was calculated as a static contact angle of water on the polymer.

(4) Glass Transition Temperature

Approximately 10 mg of a copolymer or hydrophobic polymer (hereinafter, collectively referred to as a polymer) was placed in an aluminum sample container, and the container was hermetically sealed to obtain a measurement sample. As a reference, an empty aluminum container is prepared. A heating process and a cooling process were each carried out 2 cycles. Symbol 21 in FIG. 2 denotes a DSC curve and, in FIG. 2, the abscissa represents a temperature of the sample container, and the ordinate represents a difference DSC (mW) between the amount of heat applied to the measurement sample and the amount of heat applied to the reference per unit time. An onset point (24), which is an intersection of an extended line (22) of the baseline of the DSC curve and a tangent line (23) of a baseline-shifted curve, in the heating process in the second cycle was defined as a glass transition temperature of the polymer. The measurement conditions are as follows:

DSC apparatus: SIIEXSTAR6000 Differential Scanning calorimeter DSC 6200
Measurement temperature range: −20 to 200° C.
Heating rate: 10° C./min.

(5) Flat Membrane Platelet Adhesion Test Method

A double-sided tape was bonded to a polystyrene circular plate having a diameter of 18 mm, and a flat membrane cut to 0.5 cm square was fixed thereto. When the surface of the flat membrane has contaminants, scratches, folds and the like, it may be impossible to perform accurate evaluation because platelets adhere to those parts. Therefore, a flat membrane free from contaminants, scratches and folds was used. The circular plate was attached to a cylindrically cut Falcon (registered trademark) tube (18 mm in diameter, No. 2051) such that a surface bonded to the flat film was situated inside the cylinder, and a gap was filled with a parafilm. The inside of the cylindrical tube was washed with physiological saline, and then filled with physiological saline. Human venous blood was collected, and heparin then immediately added to 50 U/ml. The physiological saline in the cylindrical tube was discarded, 1.0 ml of the blood was then placed in the cylindrical tube and shaken at 37° C. for 1 hour within 10 minutes after collection of the blood. Thereafter, the flat membrane was washed with 10 ml of physiological saline, blood components were immobilized with 2.5% glutaraldehyde physiological saline, and the flat membrane washed with 20 ml of distilled water. The washed flat membrane was dried under reduced pressure at 20° C. and 0.5 Torr for 10 hours. The flat membrane was bonded to a sample stand of a scanning electron microscope with a double-sided tape. Thereafter, a thin membrane of Pt—Pd was formed on the flat membrane surface by sputtering to prepare a sample. The surface of the flat membrane was observed with a field emission type scanning electron microscope (S800 manufactured by Hitachi, Ltd.) at a magnification of 1500 times, and the number of adhering platelets per visual field (4.3× $10^3$ μm$^2$) counted. When 50 or more platelets adhered, the number of adhering platelets was set to 50 with the membrane considered to have no platelet adhesion suppressing effect. The average of the numbers of adhering platelets in 20 different visual fields in the vicinity of the center of the flat membrane was defined as the number of adhering platelets (number/4.3×$10^3$ μm$^2$). In medical membranes other than flat membranes, a surface of a material may be appropriately exposed, and brought into contact with the blood, followed by counting the number of adhering platelets. In addition, when an electron microscope having a different visual field area, conversion may be appropriately performed to obtain the number of adhering platelets (number/4.3×$10^3$ μm$^2$).

(6) Measurement of Relative Adhesion Amount of Total Proteins 4 mL of human fresh blood containing 15% of an ACD-A solution was circulated through the hollow fiber membrane module at a flow rate of 1 mL/min for 1 hour. The hollow fiber membrane module was washed for 20 minutes by feeding a phosphate buffer solution (PBS) therethrough, and a follow fiber membrane was then cut out by 10 cm from the hollow fiber membrane module, finely cut to an about 2 mm length, and placed in an Eppendorf tube. Washing was performed with PBS (1 mL×3 times, washing was repeated when blood remained). Moisture was removed, 1 mL of a BCA reagent was then added, and the mixture immediately stirred with a micro mixer at room temperature for 2 hours. The color-developed BCA reagent was taken out into a cuvette with Pipetman, and the absorbance measured at 562 nm. The calibration curve sample (Albumin standard (manufactured by Wako Pure Chemical Industries, Ltd.) was diluted with raw food, and adjusted to 31.25 to 2000 µg/ml) was measured in the same manner as described above. From the absorbance of the calibration curve sample, the adhesion amount Tps of total proteins in the target sample was determined.

From the adhesion amount Tpc of the control (Trelite (registered trademark) CX) and the adhesion amount Tps of the target sample, the relative adhesion amount of total proteins (%) was determined in accordance with the following formula:

relative adhesion amount of total proteins (%)=$Tps/Tpc\times100$.

When the relative adhesion amount of total proteins is measured for a membrane other than a hollow fiber membrane, 4 mL of human fresh blood is brought into contact with the functional layer of the sample for 1 hour by a method such as immersion in blood, and the sample washed using a phosphate buffer solution (PBS). Thereafter, the absorbance is measured in the same manner as in the hollow fiber membrane, and the relative adhesion amount of total proteins calculated. A material before immobilization of the copolymer on the surface is used for the control.

Method of Producing Flat Membrane

A 5 µm-thick polystyrene film (manufactured by PS Japan Co., Ltd.) was shaped into a disk having a radius of 1 cm on a hot plate, and placed in a 15 mL centrifuge tube (manufactured by AS ONE Corporation). The centrifuge tube was filled with a copolymer or polymer aqueous solution having a concentration of 10 ppm, covered with a lid, and irradiated with a γ-ray of 25 kGy to obtain a flat membrane. The static contact angle of water on polystyrene corresponding to a hydrophobic polymer was 90 degrees, and the glass transition temperature of the polystyrene was 100° C.

Example 1

A vinylpyrrolidone/vinyl hexanoate random copolymer was prepared by the following method. 16.2 g of a vinylpyrrolidone monomer (manufactured by Wako Pure Chemical Industries, Ltd.), 20.8 g of a vinyl hexanoate monomer (manufactured by Tokyo Chemical Industry Co., Ltd.), 56 g of isopropanol (manufactured by Wako Pure Chemical Industries, Ltd.) as a polymerization solvent, and 0.35 g of azobisdimethylbutyronitrile as a polymerization initiator were mixed, and the mixture stirred at 70° C. for 8 hours under a nitrogen atmosphere. The reaction liquid was cooled to room temperature, concentrated, and the concentration residue was put in hexane. The precipitated white precipitate was recovered, and dried under reduced pressure at 50° C. for 12 hours to obtain 25.0 g of a vinylpyrrolidone/vinyl hexanoate random copolymer. The result of $^1$H-NMR measurement showed that the molar fraction of the vinylpyrrolidone unit was 60%. The result of GPC measurement showed that the number average molecular weight was 2,200. The static contact angle of water on the prepared copolymer was 65 degrees, and the glass transition temperature of the copolymer was 50° C. A flat membrane was prepared using the prepared vinylpyrrolidone/vinyl hexanoate random copolymer, and the number of platelet adhering to the flat membrane was 2. The shaking time was extended to 6 hours, and the number of adhering platelets was measured. The result showed that the number of adhering platelets was 3.

Example 2

A flat membrane was prepared in the same manner as in Example 1 except that a vinylpyrrolidone/vinyl propanoate random copolymer (vinylpyrrolidone unit molar fraction: 60%, number average molecular weight: 11,900, static contact angle of water: 38 degrees, glass transition temperature: 84° C.) was used in place of the vinylpyrrolidone/vinyl hexanoate random copolymer, and the number of adhering platelets was measured. The number of adhering platelets was 1. The shaking time was extended to 6 hours, and the number of adhering platelets was measured. The result showed that the number of adhering platelets was 1.

Example 3

A flat membrane was prepared in the same manner as in Example 1 except that a vinylpyrrolidone/vinyl butyrate random copolymer (vinylpyrrolidone unit molar fraction: 60%, number average molecular weight: 2,100, static contact angle of water: 50 degrees, glass transition temperature: 55° C.) was used in place of the vinylpyrrolidone/vinyl hexanoate random copolymer, and the number of adhering platelets was measured. The number of adhering platelets was 0.

Example 4

A flat membrane was prepared in the same manner as in Example 1 except that a vinylpyrrolidone/vinyl 2-ethyl hexanoate random copolymer (vinylpyrrolidone unit molar fraction: 80%, number average molecular weight: 4,500, static contact angle of water: 63 degrees, glass transition temperature: 75° C.) was used in place of the vinylpyrrolidone/vinyl hexanoate random copolymer, and the number of adhering platelets was measured. The number of adhering platelets was 3.

Example 5

A flat membrane was prepared in the same manner as in Example 1 except that a N-isopropyl acrylamide/ethyl acrylate random copolymer (N-isopropyl acrylamide unit molar fraction: 50%, number average molecular weight, static contact angle of water: 45 degrees, glass transition temperature: 72° C.) was used in place of the vinylpyrrolidone/vinyl hexanoate random copolymer, and the number of adhering platelets was measured. The number of adhering platelets was 1. The shaking time was extended to 6 hours, and the number of adhering platelets was measured. The result showed that the number of adhering platelets was 2.

Comparative Example 1

A flat membrane was prepared in the same manner as in Example 1 except that pure water was used in place of the vinylpyrrolidone/vinyl hexanoate random copolymer aqueous solution, and the number of adhering platelets was measured. The result showed that the number of adhering platelets was 50. The shaking time was extended to 6 hours, and the number of adhering platelets was measured. The result showed that the number of adhering platelets was 50.

Comparative Example 2

A flat membrane was prepared in the same manner as in Example 1 except that polyvinylpyrrolidone (K90 manufactured by BASF SE, static contact angle of water: 11 degrees, glass transition temperature: 176° C.) was used in place of the vinylpyrrolidone/vinyl hexanoate random copolymer, and the number of adhering platelets was measured. The result showed that the number of adhering platelets was 40.

Comparative Example 3

A flat membrane was prepared in the same manner as in Example 1 except that a vinylpyrrolidone/vinyl acetate random copolymer (LUVISKOL (registered trademark) VA73W manufactured by BASF SE, vinylpyrrolidone unit molar fraction: 70%, static contact angle of water: 15 degrees, glass transition temperature: 117° C.) was used in place of the vinylpyrrolidone/vinyl hexanoate random copolymer, and the number of adhering platelets was measured. The result showed that the number of adhering platelets was 30.

Comparative Example 4

A flat membrane was prepared in the same manner as in Example 1 except that a vinylpyrrolidone/styrene random copolymer (manufactured by ISP Co., Ltd., vinylpyrrolidone unit molar fraction: 90%, static contact angle of water: 40 degrees, glass transition temperature: 161° C.) was used in place of the vinylpyrrolidone/vinyl hexanoate random copolymer, and the number of adhering platelets was measured. The result showed that the number of adhering platelets was 50.

Comparative Example 5

A flat membrane was prepared in the same manner as in Example 1 except that a vinylpyrrolidone/styrene graft copolymer (manufactured by Nippon Shokubai Co., Ltd., vinylpyrrolidone unit molar fraction: 50%, static contact angle of water: 65 degrees, glass transition temperature: 100° C.) was used in place of the vinylpyrrolidone/vinyl hexanoate random copolymer, and the number of adhering platelets was measured. The result showed that the number of adhering platelets was 50.

Comparative Example 6

The polystyrene film was immersed in a chloroform solution of polyvinyl chloride (manufactured by Wako Pure Chemical Industries, Ltd., static contact angle of water: 83 degrees, glass transition temperature: 87° C.) at a concentration of 0.1% by weight, then taken out, and placed in a centrifuge tube filled with pure water, and the centrifuge tube was covered with a lid, and irradiated with a γ ray of 25 kGy to obtain a flat membrane. A platelet adhesion test was conducted, and the result showed that the number of adhering platelets was 30.

Comparative Example 7

The polystyrene film was immersed in a methanol solution of poly(2-hydroxyethyl methacrylate) (P3932 manufactured by Sigma-Aldrich Co. LLC, culture tested, static contact angle of water: 26 degrees, glass transition temperature: 55° C.) at a concentration of 0.1% by weight, then taken out, and placed in a centrifuge tube filled with pure water, and the centrifuge tube was covered with a lid, and irradiated with a γ ray of 25 kGy to obtain a flat membrane. A platelet adhesion test was conducted, and the result showed that the number of adhering platelets was 24.

Comparative Example 8

The polystyrene film was immersed in a methanol solution of polyvinyl acetate (number average molecular weight: 4,600, static contact angle of water: 60 degrees, glass transition temperature: 34° C.) at a concentration of 50% by weight in place of the vinylpyrrolidone/vinyl hexanoate random copolymer, then taken out, and placed in a centrifuge tube filled with pure water, and the centrifuge tube was covered with a lid, and irradiated with a γ ray of 25 kGy to obtain a flat membrane. The number of adhering platelets was measured, and the result showed that the number of adhering platelets was 23.

TABLE 1

| | Polymer | Static contact angle of water (degrees) | Glass transition temperature (° C.) | Hydrophilic unit | Hydrophobic unit | Hydrophilic unit ratio (%) | Number of adhering platelets (number) |
|---|---|---|---|---|---|---|---|
| Example 1 | Vinylpyrrolidone/vinyl hexanoate random copolymer | 65 | 50 | Vinylpyrrolidone | Hexanoic acid vinyl ester | 60 | 2 |
| Example 2 | Vinylpyrrolidone/vinyl propanoate random copolymer | 38 | 84 | Vinylpyrrolidone | Propanoic acid vinyl ester | 60 | 1 |
| Example 3 | Vinylpyrrolidone/vinyl butyrate random copolymer | 50 | 55 | Vinylpyrrolidone | Butyric acid vinyl ester | 60 | 0 |
| Example 4 | Vinylpyrrolidone/vinyl 2-ethylhexanoate random copolymer | 63 | 75 | Vinylpyrrolidone | 2-Ethylhexanoic acid vinyl ester | 80 | 3 |
| Example 5 | N-isopropylacrylamide/ethyl acrylate random copolymer | 45 | 72 | N-isopropyl acrylamide | Ethyl acrylate | 50 | 1 |
| Comparative Example 1 | — | — | — | — | — | — | 50 |
| Comparative Example 2 | Polyvinylpyrrolidone | 11 | 176 | Vinylpyrrolidone | — | 100 | 40 |
| Comparative Example 3 | Vinylpyrrolidone/vinyl acetate random copolymer | 15 | 117 | Vinylpyrrolidone | Acetic acid vinyl ester | 70 | 30 |
| Comparative Example 4 | Vinylpyrrolidone/styrene random copolymer | 40 | 161 | Vinylpyrrolidone | Styrene | 90 | 50 |

TABLE 1-continued

| | Polymer | Static contact angle of water (degrees) | Glass transition temperature (° C.) | Hydrophilic unit | Hydrophobic unit | Hydrophilic unit ratio (%) | Number of adhering platelets (number) |
|---|---|---|---|---|---|---|---|
| Comparative Example 5 | Vinylpyrrolidone/styrene graft copolymer | 65 | 100 | Vinylpyrrolidone | Styrene | 50 | 50 |
| Comparative Example 6 | Polyvinyl chloride | 83 | 87 | — | Vinyl chloride | 0 | 30 |
| Comparative Example 7 | Poly(2-hydroxyethyl methacrylate) | 26 | 55 | 2-hydroxyethyl methacrylate | — | 100 | 24 |
| Comparative Example 8 | Polyvinyl acetate | 60 | 34 | — | Acetic acid vinyl ester | 0 | 23 |

Method of Producing Hollow Fiber Membrane Module 16 parts by weight of polysulfone (Udel-P 3500 manufactured by Amoco Co., Ltd.), 2 parts by weight of polyvinylpyrrolidone (K30 manufactured by International Special Products Co., Ltd.; hereinafter, abbreviated as ISP Co., Ltd.) and 2 parts by weight of polyvinylpyrrolidone (K90 manufactured by ISP Co., Ltd.) were dissolved in 79 parts of N,N-dimethylacetamide and 1 part of water by heating to obtain a membrane formation dope solution.

This membrane formation dope solution was discharged through an outer tube of an orifice-type double cylindrical die having an outer diameter of 0.3 mm and an inner diameter of 0.2 mm at the annular slit portion. As a bore fluid, a solution composed of 60 parts by weight of N,N-dimethylacetamide and 40 parts by weight of water was discharged from the inside tube. The discharged membrane formation dope solution passed through a dry zone atmosphere having a dry length of 350 mm, a temperature of 30° C. and a relative humidity of 78% RH, and was then guided to a coagulation bath having 100% of water and a temperature of 40° C., and subjected to a water washing step at 60 to 75° C. for 90 seconds, a drying step at 130° C. for 2 minutes, and a crimping step at 160° C. to obtain a hollow fiber membrane. The hollow fiber membrane was taken up as a bundle. The hollow fiber membrane had an inner diameter of 200 μm and an outer diameter of 280 μm. 50 hollow fibers were inserted into a plastic tube, and the plastic tube fixed at both ends with an adhesive to prepare a hollow fiber membrane module having an effective length of 100 mm. The static contact angle of water on polysulfone corresponding to a hydrophobic polymer was 90 degrees, and the glass transition temperature of the polysulfone was 190° C.

An aqueous ethanol solution of the copolymer (300 ppm) was fed from a blood-side inlet (44A) to a dialysate-side inlet (45A) of the hollow fiber membrane module (FIG. 3). Thereafter, the hollow fiber membrane module was irradiated with a γ-ray of 25 kGy, and used as a hollow fiber membrane module.

Example 6

A hollow fiber membrane module was prepared using the vinylpyrrolidone/vinyl hexanoate random copolymer described in Example 1. Blood was fed through the obtained hollow fiber membrane module for 1 hour, and the relative adhesion amount of total proteins adhering to the membrane was measured. As shown in Table 2, the relative adhesion amount of total proteins was 9%, and it was shown that adhesion of proteins was considerably suppressed.

Example 7

A hollow fiber membrane module was prepared using the vinylpyrrolidone/vinyl propanoate random copolymer described in Example 2. Blood was fed through the obtained hollow fiber membrane module for 1 hour, and the relative adhesion amount of total proteins adhering to the membrane was measured. As shown in Table 2, the relative adhesion amount of total proteins was 5%, and it was shown that adhesion of proteins was considerably suppressed.

Example 8

A hollow fiber membrane module was prepared using the vinylpyrrolidone/vinyl butyrate random copolymer described in Example 3. Blood was fed through the obtained hollow fiber membrane module for 1 hour, and the relative adhesion amount of total proteins adhering to the membrane measured. As shown in Table 2, the relative adhesion amount of total proteins was 19%, and it was shown that adhesion of proteins was suppressed.

Example 9

A hollow fiber membrane module was prepared using a vinylpyrrolidone/vinyl butyrate random copolymer (vinylpyrrolidone unit ratio: 70%, number average molecular weight: 3,600, static contact angle of water: 39 degrees, glass transition temperature: 66° C.). Blood was fed through the obtained hollow fiber membrane module for 1 hour, and the relative adhesion amount of total proteins adhering to the membrane measured. As shown in Table 2, the relative adhesion amount of total proteins was 15%, and it was shown that adhesion of proteins was suppressed.

Example 10

A hollow fiber membrane module was prepared using the N-isopropylacrylamide/ethyl acrylate random copolymer (100 ppm) described in Example 5. Blood was fed through the obtained hollow fiber membrane module for 1 hour, and the relative adhesion amount of total proteins adhering to the membrane measured. As shown in Table 2, the relative adhesion amount of total proteins was 10%, and it was shown that adhesion of proteins was considerably suppressed.

Comparative Example 9

A hollow fiber membrane module was prepared using the polyvinylpyrrolidone described in Comparative Example 2. Blood was fed through the obtained hollow fiber membrane module for 1 hour, and the relative adhesion amount of total proteins adhering to the membrane measured. As shown in Table 2, the relative adhesion amount of total proteins was 88%, and it was shown that adhesion of a large amount of proteins occurred.

Comparative Example 10

A hollow fiber membrane module was prepared using a vinylpyrrolidone/vinyl acetate random copolymer (manufactured by BASF SE, vinylpyrrolidone unit ratio: 50%, static contact angle of water: 25 degrees, glass transition temperature: 96° C.). Blood was fed through the obtained hollow fiber membrane module for 1 hour, and the relative adhesion amount of total proteins adhering to the membrane measured. As shown in Table 2, the relative adhesion amount of total proteins was 65%, and it was shown that adhesion of a large amount of proteins occurred.

Comparative Example 11

A hollow fiber membrane module was prepared using a vinylpyrrolidone/vinyl acetate block copolymer (vinylpyrrolidone unit ratio: 60%, number average molecular weight: 4,600, static contact angle of water: 55 degrees, two glass transition temperatures: 35° C. and 140° C.). Blood was fed through the obtained hollow fiber membrane module for 1 hour, and the relative adhesion amount of total proteins adhering to the membrane was measured. As shown in Table 2, the relative adhesion amount of total proteins was 78%, and it was shown that adhesion of a large amount of proteins occurred.

Comparative Example 12

A hollow fiber membrane module was prepared using an aqueous solution of a vinylpyrrolidone/vinyl acetate random copolymer (manufactured by BASF SE, vinylpyrrolidone unit ratio: 60%, number average molecular weight: 3,900, static contact angle of water: 18 degrees, glass transition temperature: 110° C.) at a concentration of 10 ppm. Blood was fed through the obtained hollow fiber membrane module for 1 hour, and the relative adhesion amount of total proteins adhering to the membrane measured. As shown in Table 2, the relative adhesion amount of total proteins was 80%, and it was shown that adhesion of a large amount of proteins occurred.

Comparative Example 13

A hollow fiber membrane module was prepared using a vinylpyrrolidone/vinyl propanoate block copolymer (vinylpyrrolidone unit ratio: 60%, number average molecular weight: 4,100, static contact angle of water: 57 degrees, two glass transition temperatures: 20° C. and 135° C.). Blood was fed through the obtained hollow fiber membrane module for 1 hour, and the relative adhesion amount of total proteins adhering to the membrane measured. As shown in Table 2, the relative adhesion amount of total proteins was 48%, and it was shown that adhesion of a large amount of proteins occurred.

Comparative Example 14

A hollow fiber membrane module was prepared using a vinylpyrrolidone/vinyl butyrate random copolymer (vinylpyrrolidone unit ratio: 60%, number average molecular weight: 600, static contact angle of water: 41 degrees, glass transition temperature: 25° C.). Blood was fed through the obtained hollow fiber membrane module for 1 hour, and the relative adhesion amount of total proteins adhering to the membrane measured. As shown in Table 2, the relative adhesion amount of total proteins was 73%, and it was shown that adhesion of a large amount of proteins occurred.

Comparative Example 15

A hollow fiber membrane module was prepared using a vinylpyrrolidone/vinyl butyrate random copolymer (vinylpyrrolidone unit ratio: 90%, number average molecular weight: 8,600, static contact angle of water: 29 degrees, glass transition temperature: 146° C.). Blood was fed through the obtained hollow fiber membrane module for 1 hour, and the relative adhesion amount of total proteins adhering to the membrane was measured. As shown in Table 2, the relative adhesion amount of total proteins was 81%, and it was shown that adhesion of a large amount of proteins occurred.

TABLE 2

| | Polymer | Static contact angle of water (degrees) | Glass transition temperature (° C.) | Hydrophilic unit | Hydrophobic unit | Hydrophilic unit ratio (%) | Relative adhesion amount of total proteins (%) |
|---|---|---|---|---|---|---|---|
| Example 6 | Vinylpyrrolidone/vinyl hexanoate random copolymer | 65 | 50 | Vinylpyrrolidone | Hexanoic acid vinyl ester | 60 | 9 |
| Example 7 | Vinylpyrrolidone/vinyl propanoate random copolymer | 38 | 84 | Vinylpyrrolidone | Propanoic acid vinyl ester | 60 | 5 |
| Example 8 | Vinylpyrrolidone/vinyl butyrate random copolymer | 50 | 55 | Vinylpyrrolidone | Butyric acid vinyl ester | 60 | 19 |
| Example 9 | Vinylpyrrolidone/vinyl butyrate random copolymer | 39 | 66 | Vinylpyrrolidone | Butyric acid vinyl ester | 70 | 15 |
| Example 10 | N-isopropylacrylamide/ethyl acrylate random copolymer | 45 | 72 | N-isopropyl acrylamide | Ethyl acrylate | 50 | 10 |
| Comparative Example 9 | Polyvinylpyrrolidone | 11 | 176 | Vinylpyrrolidone | — | 100 | 88 |
| Comparative Example 10 | Vinylpyrrolidone/vinyl acetate random copolymer | 25 | 96 | Vinylpyrrolidone | Acetic acid vinyl ester | 50 | 65 |
| Comparative Example 11 | Vinylpyrrolidone/vinyl acetate block copolymer | 55 | 35, 140 | Vinylpyrrolidone | Acetic acid vinyl ester | 60 | 78 |
| Comparative Example 12 | Vinylpyrrolidone/vinyl acetate random copolymer | 18 | 110 | Vinylpyrrolidone | Acetic acid vinyl ester | 60 | 80 |
| Comparative Example 13 | Vinylpyrrolidone/vinyl propanoate block copolymer | 57 | 20, 135 | Vinylpyrrolidone | Propanoic acid vinyl ester | 60 | 48 |

TABLE 2-continued

|  | Polymer | Static contact angle of water (degrees) | Glass transition temperature (° C.) | Hydrophilic unit | Hydrophobic unit | Hydrophilic unit ratio (%) | Relative adhesion amount of total proteins (%) |
|---|---|---|---|---|---|---|---|
| Comparative Example 14 | Vinylpyrrolidone/vinyl butyrate random copolymer | 41 | 25 | Vinylpyrrolidone | Butyric acid vinyl ester | 60 | 73 |
| Comparative Example 15 | Vinylpyrrolidone/vinyl butyrate random copolymer | 29 | 146 | Vinylpyrrolidone | Butyric acid vinyl ester | 90 | 81 |

In Table 2, the "static contact angle of water" indicates the static contact angle of water on a homopolymer or copolymer, and the "glass transition temperature" indicates the glass transition temperature of a homopolymer or copolymer.

INDUSTRIAL APPLICABILITY

The medical material is excellent in biocompatibility, and capable of suppressing adhesion of platelets and proteins and, therefore, can be used for a long period of time. Thus, the medical material can be used as a medical separation membrane to be used for medical devices such as blood purifiers.

The invention claimed is:

1. A medical separation membrane, a blood circuit, a blood storage bag, a catheter, a stent, a contact lens or a biosensor in which a medical material is bonded or attached to a surface of a membrane including a hydrophobic polymer,
wherein the medical material is a copolymer comprising a hydrophobic unit and a hydrophilic unit,
the hydrophobic unit has a terminal alkyl group having 2 to 20 carbon atoms in a side chain,
a static contact angle of water on the copolymer is 30 degrees or more and less than 70 degrees, and
the copolymer has only one glass transition temperature of 45° C. or higher and lower than 90° C.

2. The medical material according to claim 1, wherein the hydrophobic unit is an alkyl carboxylic acid vinyl ester unit.

3. The medical material according to claim 1, wherein the hydrophilic unit is a vinylpyrrolidone unit.

4. The medical material according to claim 1, wherein the static contact angle of water on the copolymer is 34 degrees or more and less than 50 degrees, and
the copolymer has only one glass transition temperature of 70° C. or higher and lower than 88° C.

5. The medical separation membrane according to claim 4, wherein
the static contact angle of water on the hydrophobic polymer is 70 degrees or more and less than 160 degrees, and
the glass transition temperature of the hydrophobic polymer is 50° C. or higher and lower than 250° C.

6. The medical separation membrane according to claim 4, wherein the hydrophobic polymer includes a polymer selected from the group consisting of a polysulfone-based polymer, a polymethacrylate-based polymer, a polyacrylate-based polymer, a polyester-based polymer and a polystyrene-based polymer.

7. A blood purifier including the medical separation membrane according to claim 4.

8. The medical material according to claim 2, wherein the hydrophilic unit is a vinylpyrrolidone unit.

9. The medical material according to claim 2, wherein
the static contact angle of water on the copolymer is 34 degrees or more and less than 50 degrees, and
the copolymer has only one glass transition temperature of 70° C. or higher and lower than 88° C.

10. The medical material according to claim 3, wherein
the static contact angle of water on the copolymer is 34 degrees or more and less than 50 degrees, and
the copolymer has only one glass transition temperature of 70° C. or higher and lower than 88° C.

11. A medical separation membrane in which the medical material according to claim 2 is bonded or attached to a surface of a membrane including a hydrophobic polymer.

12. A medical separation membrane in which the medical material according to claim 3 is bonded or attached to a surface of a membrane including a hydrophobic polymer.

13. A medical separation membrane in which the medical material according to claim 4 is bonded or attached to a surface of a membrane including a hydrophobic polymer.

14. The medical separation membrane according to claim 5, wherein the hydrophobic polymer includes a polymer selected from the group consisting of a polysulfone-based polymer, a polymethacrylate-based polymer, a polyacrylate-based polymer, a polyester-based polymer and a polystyrene-based polymer.

15. A blood purifier including the medical separation membrane according to claim 5.

16. A blood purifier including the medical separation membrane according to claim 6.

* * * * *